(12) United States Patent
Raghavan et al.

(10) Patent No.: US 11,654,185 B2
(45) Date of Patent: May 23, 2023

(54) USE OF HYALURONIDASE FOR TREATMENT OF MUSCLE STIFFNESS

(71) Applicant: New York University, New York, NY (US)

(72) Inventors: Preeti Raghavan, Brooklyn, NY (US); Antonio Stecco, Padua (IT)

(73) Assignee: New York University, New York, NY (US)

( * ) Notice: Subject to any disclaimer, the term of this patent is extended or adjusted under 35 U.S.C. 154(b) by 55 days.

(21) Appl. No.: 16/429,272

(22) Filed: Jun. 3, 2019

(65) Prior Publication Data

US 2019/0282674 A1   Sep. 19, 2019

Related U.S. Application Data

(62) Division of application No. 15/325,938, filed as application No. PCT/US2015/040767 on Jul. 16, 2015, now Pat. No. 10,307,467.

(60) Provisional application No. 62/118,707, filed on Feb. 20, 2015, provisional application No. 62/025,257, filed on Jul. 16, 2014.

(51) Int. Cl.
```
A61K 38/47    (2006.01)
A61P 21/02    (2006.01)
A61K 9/00     (2006.01)
A61K 47/02    (2006.01)
```

(52) U.S. Cl.
CPC ............ *A61K 38/47* (2013.01); *A61K 9/0019* (2013.01); *A61K 47/02* (2013.01); *A61P 21/02* (2018.01); *C12Y 302/01035* (2013.01)

(58) Field of Classification Search
None
See application file for complete search history.

(56) References Cited

U.S. PATENT DOCUMENTS

| | | | |
|---|---|---|---|
| 3,898,325 A | 8/1975 | Revici | |
| 6,009,875 A | 1/2000 | Hubbard, Jr. | |
| 9,333,244 B2* | 5/2016 | Li | A61P 43/00 |
| 9,878,046 B2 | 1/2018 | Shepard et al. | |
| 10,301,376 B2 | 5/2019 | Schiff et al. | |
| 2003/0236306 A1 | 12/2003 | Chen et al. | |
| 2004/0268425 A1* | 12/2004 | Bookbinder | A61P 19/00 |
| | | | 435/325 |
| 2005/0148935 A1 | 7/2005 | Dimitrova et al. | |
| 2006/0093624 A1 | 5/2006 | Graham | |
| 2009/0324647 A1 | 12/2009 | Borodic | |
| 2010/0196445 A1 | 8/2010 | David et al. | |
| 2011/0076273 A1* | 3/2011 | Adler | C07K 16/2887 |
| | | | 424/173.1 |
| 2013/0142770 A1 | 6/2013 | Gaylis et al. | |
| 2013/0216517 A1 | 8/2013 | Kim | |
| 2015/0010528 A1* | 1/2015 | Weg | A61K 31/137 |
| | | | 604/82 |

FOREIGN PATENT DOCUMENTS

| | | | |
|---|---|---|---|
| CA | 2468246 A1 | 6/2003 | |
| CA | 2839511 A1 | 12/2012 | |
| CN | 101961344 A | 2/2011 | |
| WO | WO-2005118799 A1 * | 12/2005 | ............... C07K 7/08 |
| WO | WO-2012174478 A2 * | 12/2012 | ............ A61K 38/28 |
| WO | 2014/069757 A1 | 5/2014 | |
| WO | WO-2014069757 A1 * | 5/2014 | |

OTHER PUBLICATIONS

Hirch, Ranelle J; et al; "Hyaluronidase in the office: A necessity for every dermasurgeon that injects hyaluronic acid" Journal of Cosmetic and Laser Therapy, 9, 182-185, 2007 (Year: 2007).*
Stecco, A., et al., Peripheral Mechanisms Contributing to Spasticity and Implications for Treatment, Curr Phys Med Rehabil Rep, Mar. 30, 2014, vol. 2, pp. 121-127.
Stecco, A., et al., Ultrasonography in myofascial neck pain: randomized clinical trial for diagnosis and follow-up, Surgical and Radiological Anatomy, 2014, vol. 36, pp. 243-253.
Liu, J. et al., Advances in the Research on Meridians One of the Preliminarily-selected Items of the State Scaling Program in "the 9th Five-years Period", Acupuncture Research, Dec. 31, 2002, vol. 27, No. 3, pp. 230-237.
Shanghai First Medical College et al., Pharmacology, First People's Medical Publishing House, Nov. 30, 1979, vol. 1, First edition, p. 265.
Zhang, B., et al., Theory and Practice of College Physical Education Health, Sun yat-sen university press, Sep. 30, 2005, First edition, p. 183.
Wu, H. et al., Evaluation on the effects of hyaluronan combined with different dosage of celecoxib for relieving pain and ankylosis induced by knee osteoarthritis, Chinese Journal of Clinical Rehabilitation, Sep. 15, 2004, vol. 8, No. 26, pp. 5491-5493.

* cited by examiner

*Primary Examiner* — David W Berke-Schlessel
(74) *Attorney, Agent, or Firm* — Hodgson Russ LLP

(57) ABSTRACT

Provided are methods and kits for reducing the severity of muscle stiffness. The method comprises delivering to one or more specific locations in the deep fascia of an affected muscle a composition comprising a therapeutically effective amount of hyaluronidase.

10 Claims, 12 Drawing Sheets

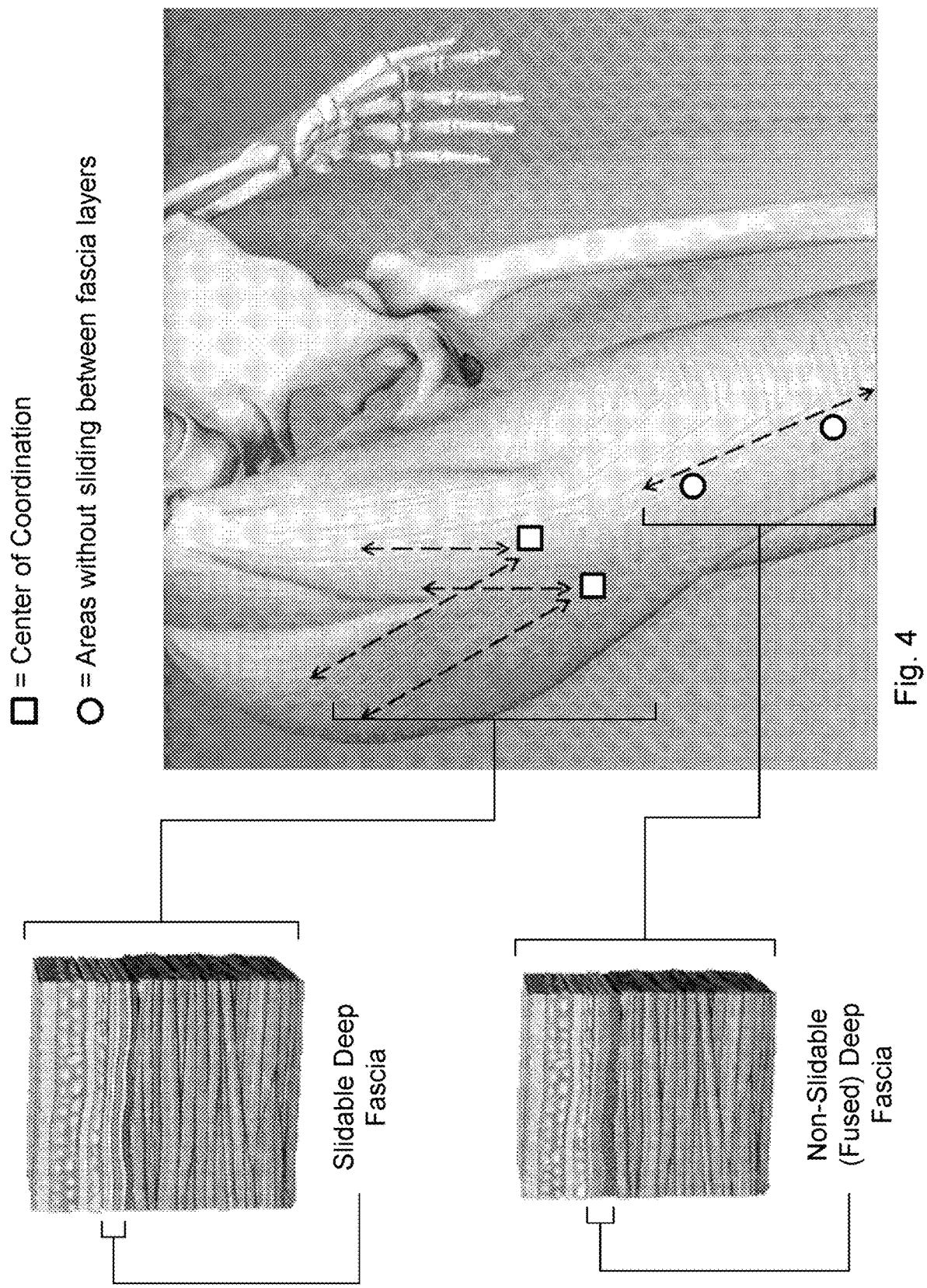

USE OF HYALURONIDASE FOR TREATMENT OF MUSCLE STIFFNESS

CROSS-REFERENCE TO RELATED APPLICATIONS

This application is a divisional of U.S. patent application Ser. No. 15/325,938, filed on Jan. 12, 2017, which is a National Phase of International application no. PCT/US2015/040767, filed on Jul. 16, 2015, which claims priority to U.S. provisional patent application No. 62/025,257, filed on Jul. 16, 2014, and to U.S. provisional patent application No. 62/118,707, filed on Feb. 20, 2015, the disclosures of each of which are incorporated herein by reference.

STATEMENT REGARDING FEDERALLY SPONSORED RESEARCH OR DEVELOPMENT

This invention was made with government support under grant no. R01 HD071978 awarded by the National Institutes of Health. The government has certain rights in the invention.

BACKGROUND OF THE DISCLOSURE

Muscle stiffness is a common symptom for which no specific etiology has been determined and no treatment exists as of yet. Muscle stiffness often occurs from lack of movement, for example after prolonged bed rest (Clavet et al., 2008, CMAJ, March 11, 178(6):691-7), in the elderly (Trindade et al., 2012, J Biomech., January 3, 45(1):199-201; Wojtysiak, 2013, Folia Biol (Krakow), 61(3-4):221-6, PubMed PMID: 24279172), with paralysis of limbs due to neurological or muscular diseases, due to metabolic conditions such as diabetes (Duffin, 2002, Diabet Med. December, 19(12):1009-13, PubMed PMID: 12647842), and after excessive exercises such as running a marathon etc. The severity of muscle stiffness can range from an uncomfortable sensation of rigidity to exacerbation of spasticity (if there is a previous central nervous system injury). Both rigidity and spasticity may be accompanied by non-specific pain. The high incidence of muscle stiffness represents an enormous cost to society worldwide.

Spasticity commonly presents as muscle over-activity, reduction in the ability to relax specific muscles, hypertonia, paresis, muscle spasms, and loss of fine motor control, attributed to neural mechanisms. However, less understood symptoms of spasticity include increased stiffness in the soft tissue, muscle fatigue, and postural changes in the limbs, which can be explained by non-neural/peripheral contributions that have secondary effects on skeletal muscles. In fact it has been shown that spasticity is not an immediate consequence of CNS injury as it progresses during the weeks and months after injury; this suggests that there are other non-neural/peripheral factors that contribute to spasticity (Lundstrom et al., 2008, Eur J Neurol., 15(6):533-9).

Surgical, pharmacological, and physiotherapy techniques are among the most common interventions offered to alleviate spasticity. Pharmacological agents include oral medication such as benzodiazepines, baclofen, tizanidine hydrochloride, and dantrolene. Diazepam is one of the oldest and most commonly used benzodiazepine for treating spasticity. Botulinum toxin type A is used for focal treatment of overly spastic muscles, while intrathecal baclofen is commonly used to reduce spasticity in individuals with spinal cord injury. However, even though current pharmacological agents significantly reduce spasticity, their use does not always translate into increased function because of side effects including drowsiness and muscle weakness (Nielsen et al., 2007, Acta Physiol (Oxf), February, 189(2):171-80).

SUMMARY OF THE DISCLOSURE

The present disclosure provides methods and kits for reducing muscle stiffness. The methods and kits are based on the observation that injection of hyaluronidase in the deep fascia region at or near specific sites—termed as the centers of coordination—results in amelioration of stiffness of muscles. In one aspect, the present disclosure provides a method for providing relief from stiffness of a muscle in an individual comprising the steps of delivering in a region of deep fascia surrounding the muscle at one or more centers of coordination (CCs) or centers of fusion (CFs) a composition comprising a therapeutically effective amount of hyaluronidase. Alternatively or additionally, hyaluronidase may be delivered to a region of deep fascia surrounding a second muscle that affects the function of the first muscle (or whose function is affected by the function of the first muscle) at or near one or more centers of coordination or center of fusion associated with the second muscle. This results in reducing stiffness of the first muscle.

The present disclosure also provides kits for reducing stiffness of muscles. The kits comprise one or more of: combined or separate doses of hyaluronidase for one or more injections, administrations aids (such as syringes), charts showing centers of coordination or center of fusion where hyaluronidase may be injected, instructions for use, and follow-up guidance. Hyaluronidase may be provided as a combined dose (in a single vial) or as multiple individual doses, and may be provided in a ready-to-use form or in a form that can be reconstituted. If provided in a form that can be reconstituted, the kit may also contain reconstitution medium.

DESCRIPTION OF THE FIGURES

FIG. 4. Illustration of region of a lower limb showing comparison of deep fascia layers of a region which has centers of coordination versus a region which does not. The deep fascia layers at a center of coordination are slidable with respect to each other, while the deep fascia layers at regions which do not have centers of coordination or center of fusion are fused and therefore are not slidable with respect to each other.

DETAILED DESCRIPTION OF THE DISCLOSURE

Figure 1A:
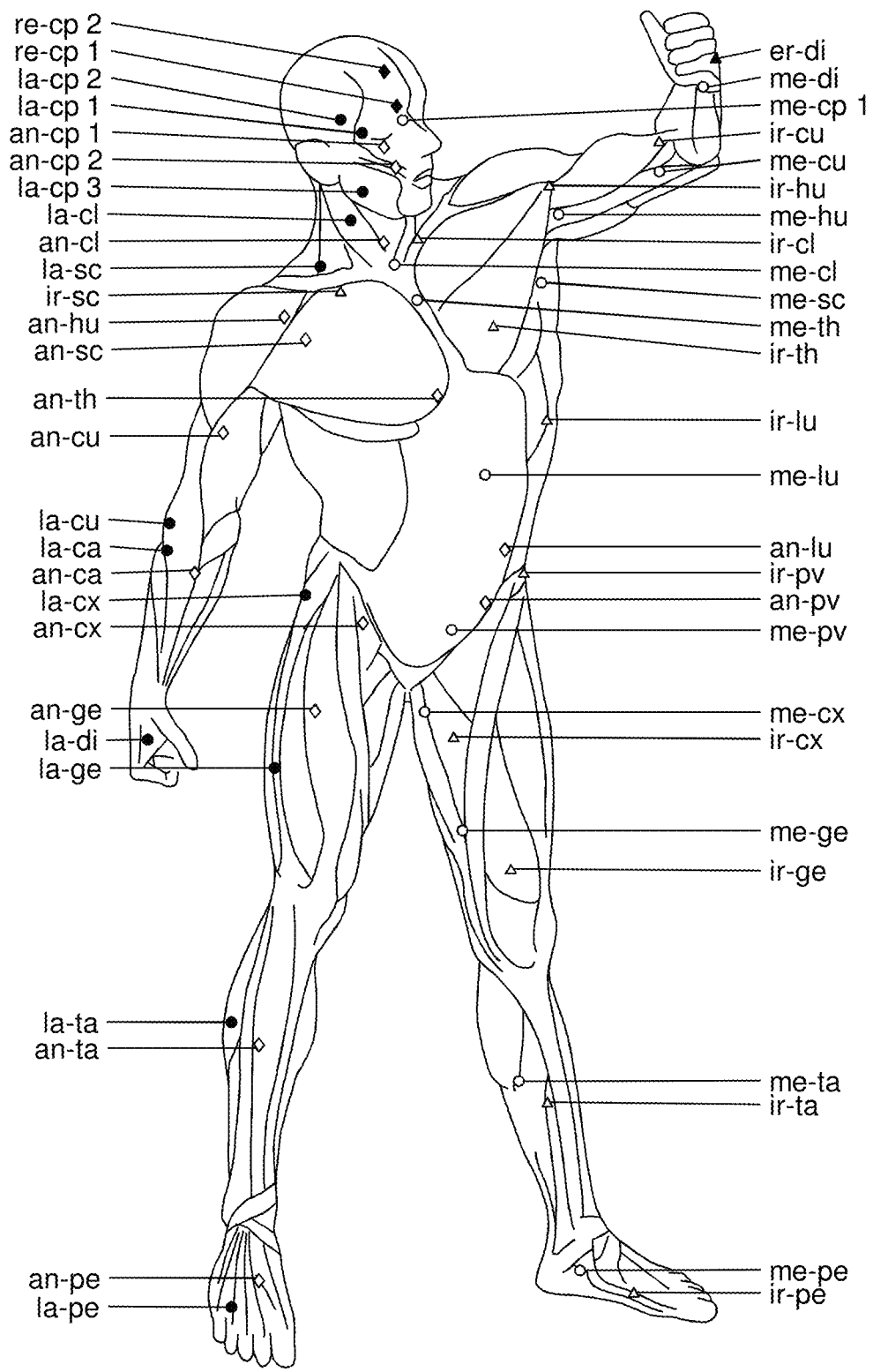
FIGS. 1A and 1B. Illustration of centers of coordination in the front and back of a human body. The various symbols represent: empty circles: anterior CCs related to movement in the frontal (or coronal) plane, filled circles: posterior CCs related to movement in the frontal plane, empty triangles: anterior CCs related to movement in the horizontal (or transverse) plane, filled triangles: posterior CCs related to movement in the horizontal plane, empty diamonds: anterior CCs related to movement in the sagittal plane, filled diamonds: posterior CCs related to movement in the sagittal plane.

The present disclosure provides a method for reducing or treating muscle stiffness with or without pain. The method can be used in neurologic patients who may have spasticity as well as in non-neurologic patients with non-specific muscle pain related to muscle stiffness. The method comprises administering compositions comprising hyaluronidase into the deep fascia region at specific locations surrounding the affected muscle. Alternatively, or additionally, hyaluronidase administrations may be carried out at specific locations in deep fascia region that surround other muscles that have an effect on the function of, or whose function is affected by, the muscle in question. Such deep fascia region of a second muscle is considered to be in continuity with the deep fascia region surrounding the affected muscle. The affected muscle is also referred to herein as the "first muscle" or the "muscle in question". The deep fascia may surround the muscles partially or completely.

The present method is based on the observation that injection of hyaluronidase at or near specific sites (centers of coordination (CCs) or centers of fusion (CFs)) results in reducing stiffness. It was also observed that hyaluronidase injection in other areas (not at or near a CC) does not result in measurable reduction of stiffness. In one embodiment, the disclosure provides a method for providing relief from stiffness of a first muscle in an individual comprising the steps of delivering in a region of deep fascia surrounding the first muscle or in a region of deep fascia surrounding a second muscle that affects (or is affected by) the function of the first muscle at or near one or more centers of coordination or centers of fusion associated with the muscle, a composition comprising a therapeutically effective amount of hyaluronidase. This results in reducing stiffness of the first muscle.

Hyaluronidase is an enzyme known to degrade hyaluronic acid. It has been approved as an adjuvant to increase the spread and dispersion of other administered drugs. Hyaluronidase is commercially available as Vitrase, Amphadase, Hydase, and Hylenex. These formulations represent hyaluronidase from ovine, bovine and human sources.

In one aspect, the present disclosure provide hyaluronidase compositions for use in reducing muscle stiffness. The compositions comprise hyaluronidase in pharmaceutically acceptable carriers (including physiological buffers) or in dry form (e.g., powdered or lyophilized). The compositions may comprise multiple doses or a single dose for administration, such as via injection, to an individual for delivery to the deep fascia region at specific locations in muscles.

In the present disclosure, hyaluronidase is delivered at or near at least one center of coordination site or at least one center of fusion site. In one embodiment, hyaluronidase is delivered to the CC sites by injections. For examples, hyaluronidase is administered by injections in 1 to 10 sites (and all integer values therebetween). In various embodiments, injections may be given at 1, 2, 3, 4, 5, 6, 7, 8, 9 or 10 sites. In one embodiment, injections are given at two or more sites. In one embodiment, injections may be given in at least 10 sites (such as from 10-20 sites). For example, to treat muscle stiffness in limbs, 6-10 sites can be injected in the limb at various CC points along the limb.

Centers of coordination represent points in the deep fascia or within muscles (perimysium, epimysium) where muscular forces converge. A Center of coordination is a region of convergence of collagen fibres originating from groups of motor units which move a segment in one specific direction in space (Stecco L. 2004, Fascial Manipulation for Musculoskeletal Pain; Piccin; April 2004, incorporated herein by reference). In one embodiment, a second group of points that could be used are the centers of fusions (CFs). The CFs are the converging points for vectors of intermediate muscular fibres of three planes in the space in the adjacent directions. (Stecco L. 2004, Fascial Manipulation for Musculoskeletal Pain; Piccin; April 2004, page 149, chapter 15) A CC site is considered to be a focal point in the deep fascia where vector forces produced by the contraction of monoarticular and biarticular muscle fibers of one body segment converge during a precise movement. Being a focal point for the convergence of numerous vectors, CCs are commonly located at a distance from the relative joint component. Stecco (2004) has mapped out the anatomical location of CCs within each body segment.

Figure 1B:
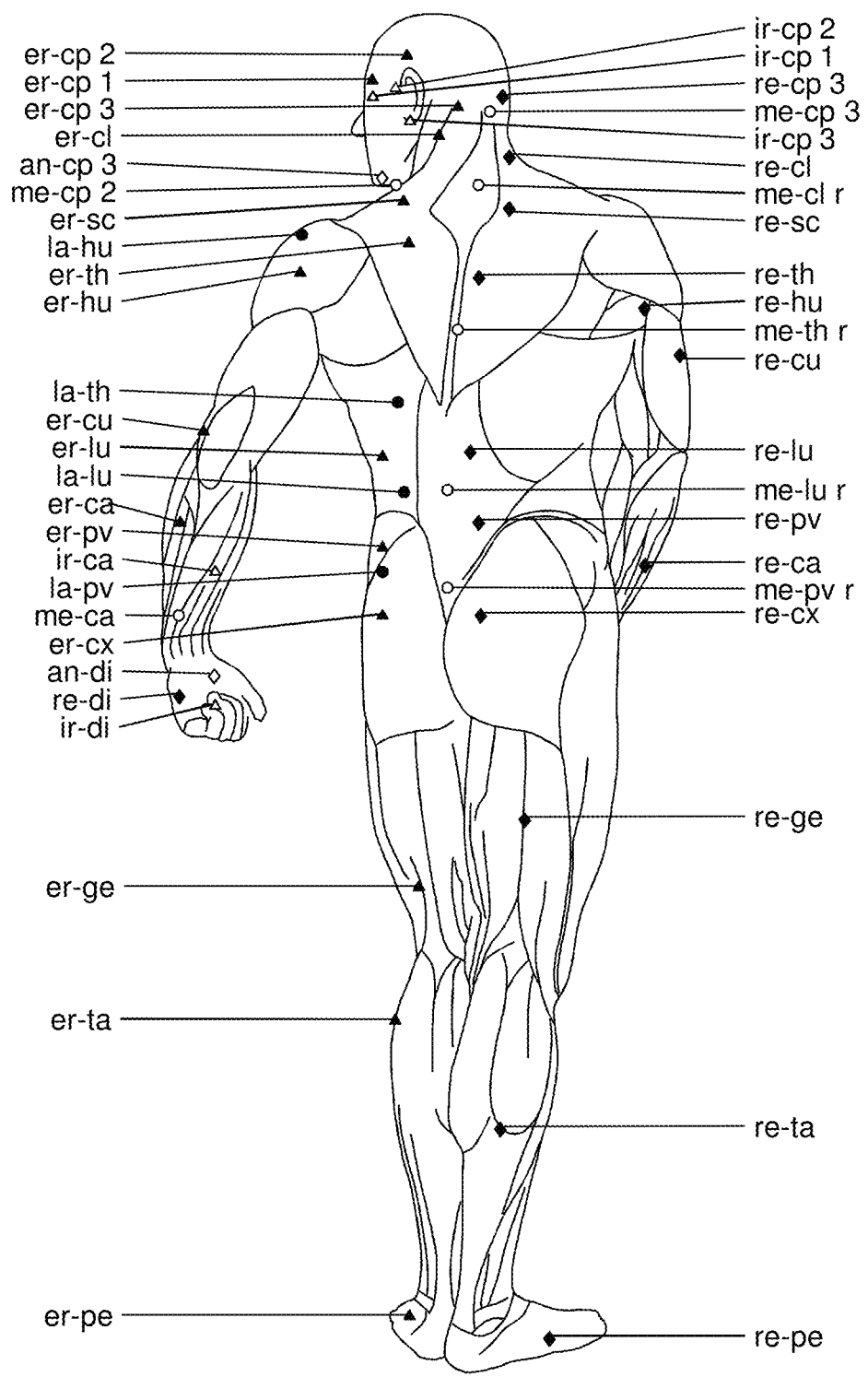
Figure 2A:
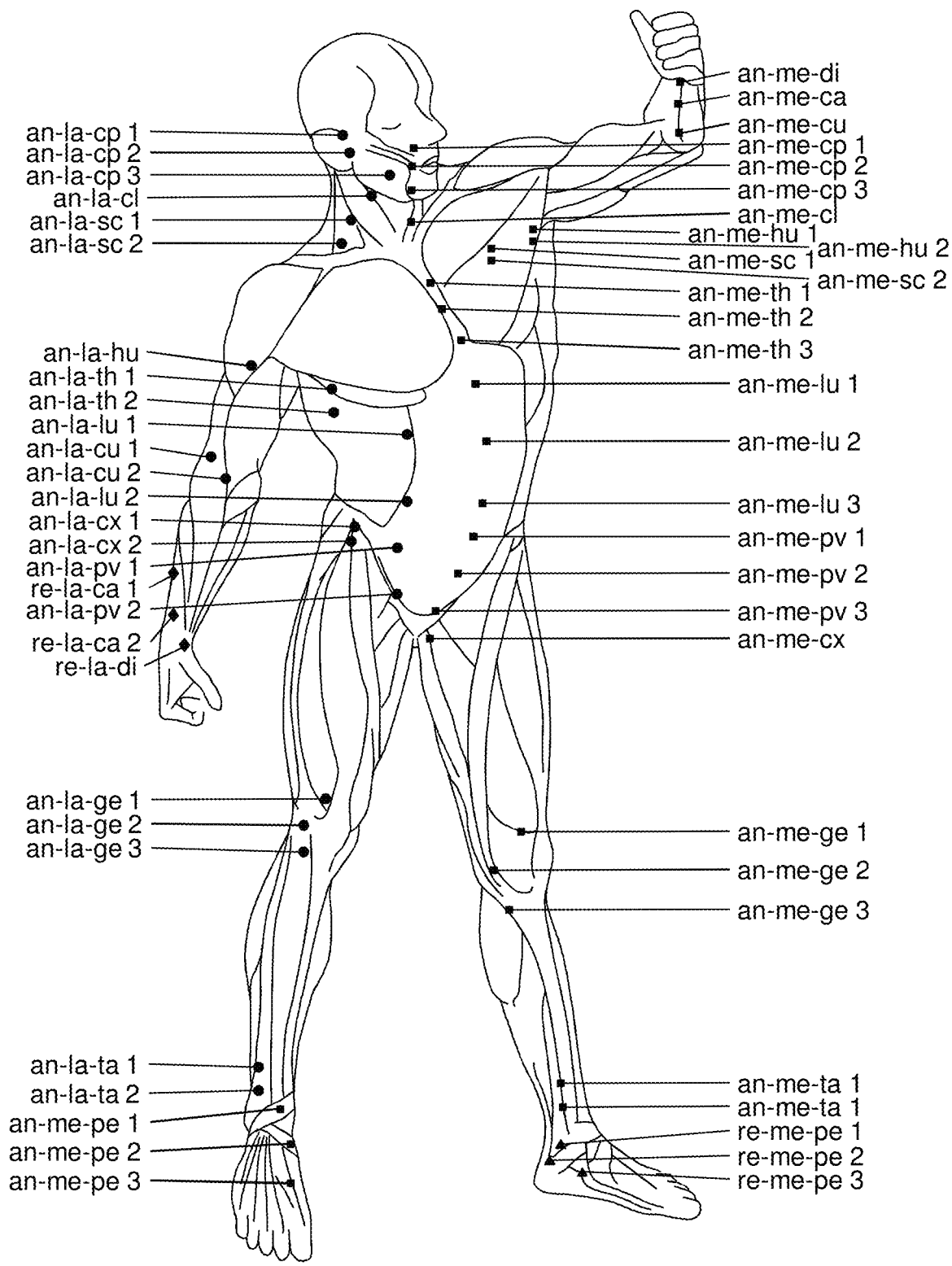
FIGS. 2A and 2B. Illustration of centers of fusion in the front and back of a human body. The various symbols represent: ante-lateral direction (circles), retro-lateral direction (diamonds), ante-medio direction (square) and retro-medio direction (triangles).
Figure 2B:
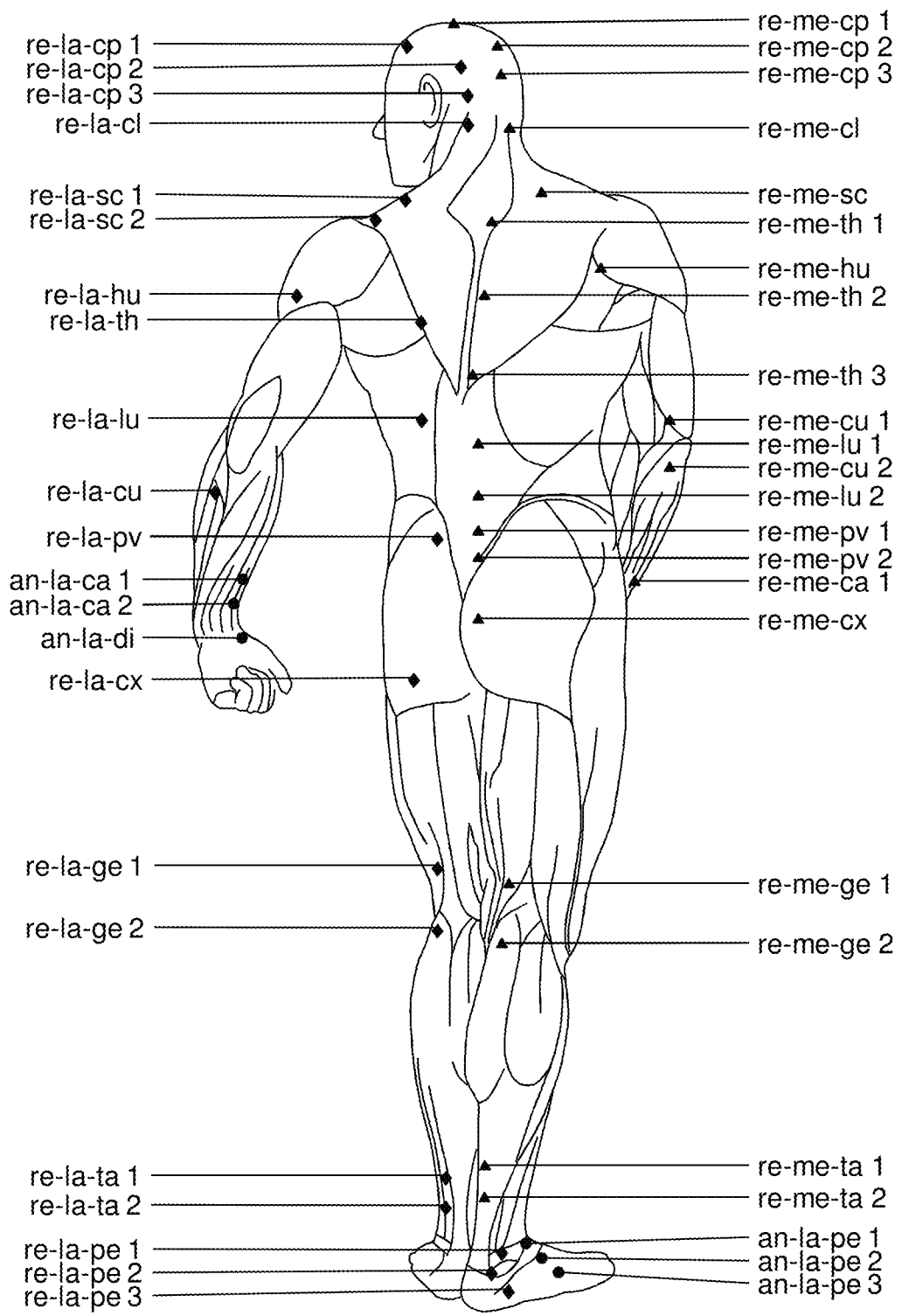

As shown in FIGS. 1A and 1B, 100 CCs have been identified. In FIGS. 2A and 2B, 105 CFs have been identified. Each CC and CF is shown as having a unique arbitrary identifier. The Center of Coordinations may be grouped based on affecting muscles that facilitate movement in the frontal plane (circles), sagittal plane (diamonds) or horizontal plane (triangles). The CCs in the front of the body are shown as empty symbols, and those in the back of the body are shown as filled symbols (FIGS. 1A and 1B). The CFs may be grouped based on affecting muscles that facilitate movement in the ante-lateral direction (circles), retro-lateral direction (diamonds), ante-medio direction (square) or retro-medio direction (triangles) (FIGS. 2A and 2B).

Figure 3A:
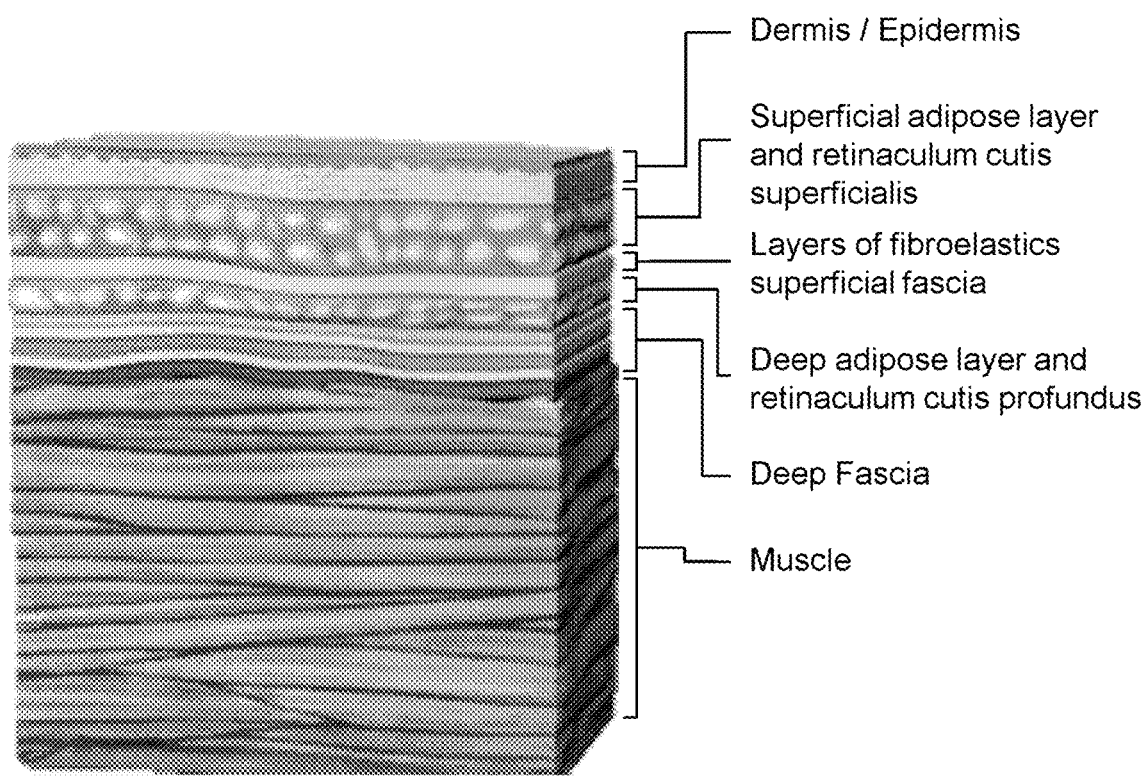
FIGS. 3A and 3B. Illustration of layers of the skin and muscles at a center of coordination. The various layers are illustrated. A thin layer of epimysium is present between the deep fascia and the muscle. The deep fascia is shown as three layers of dense connective tissue (comprising collagen fiber type I and III) and two layers of loose connective tissue (comprising adipose cells, GAG and hyaluronic acid). In 3A, the layers of the deep fascia are shown in a non-sliding position and in FIG. 3B, the layers of the fascia are shown after sliding relative to each other.
Figure 3B:
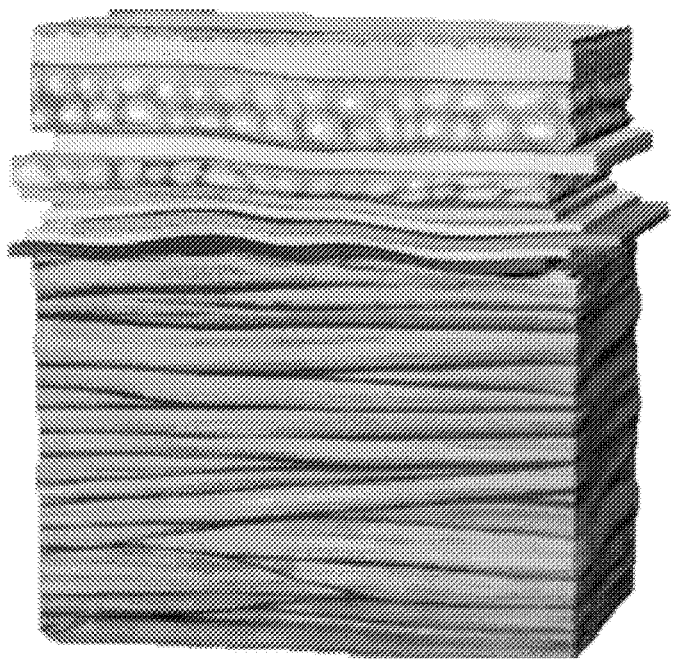
Figure 5A:
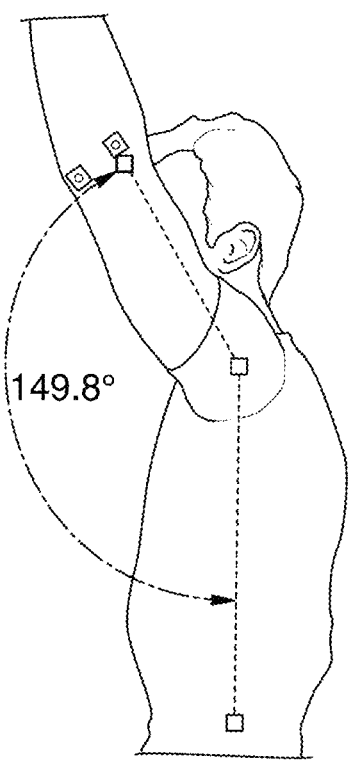
FIGS. 5A-5B, 6, 7A-7C, 8A-8C, 9A-9B, 10A-10B, 11A-11B, and 12A-12F. Illustrations of shoulder flexion/extension movements that can be used to assess restriction of movement due to muscle stiffness.
Figure 5B:
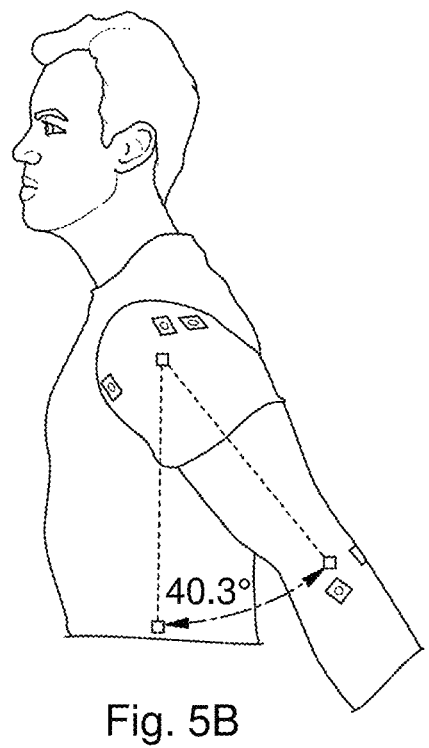
Figure 6:
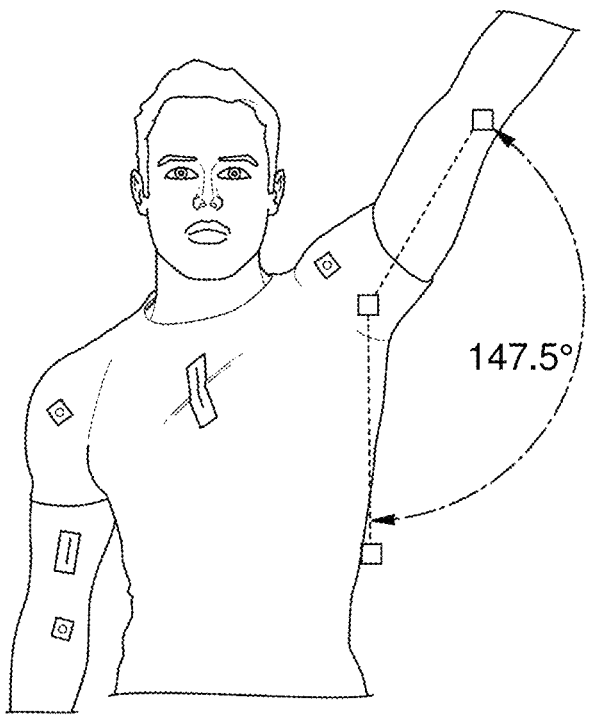
Figure 7A:
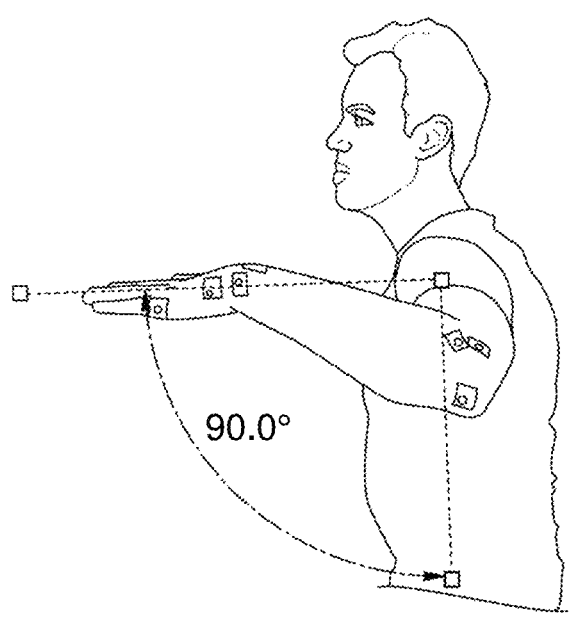
Figure 7B:
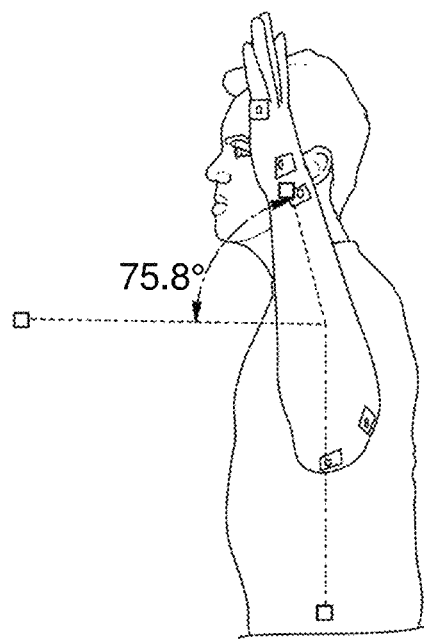
Figure 7C:
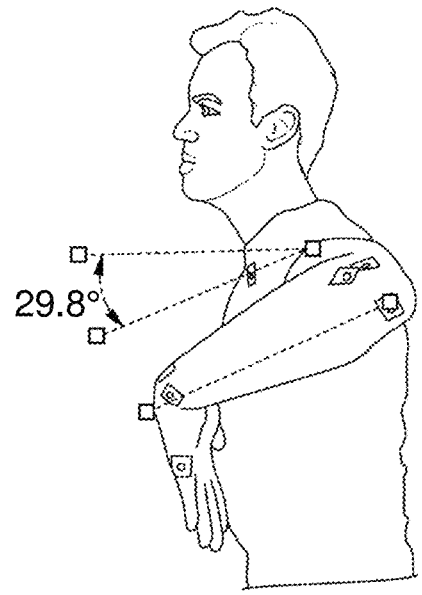
Figure 8A:
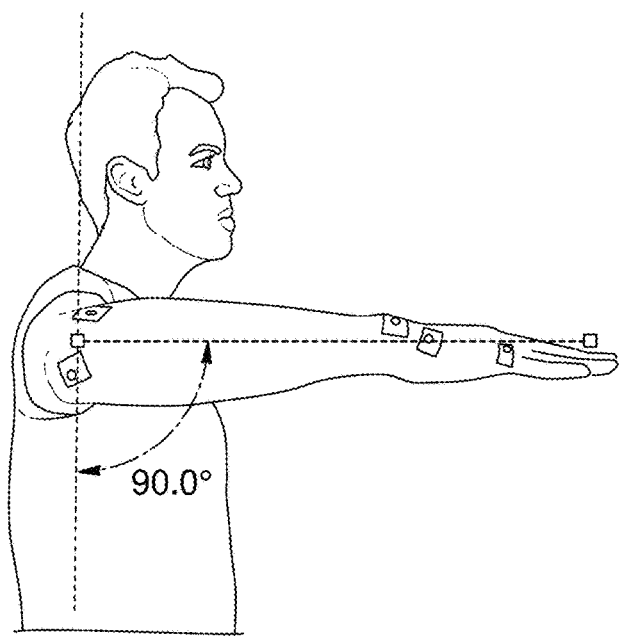
Figure 8B:
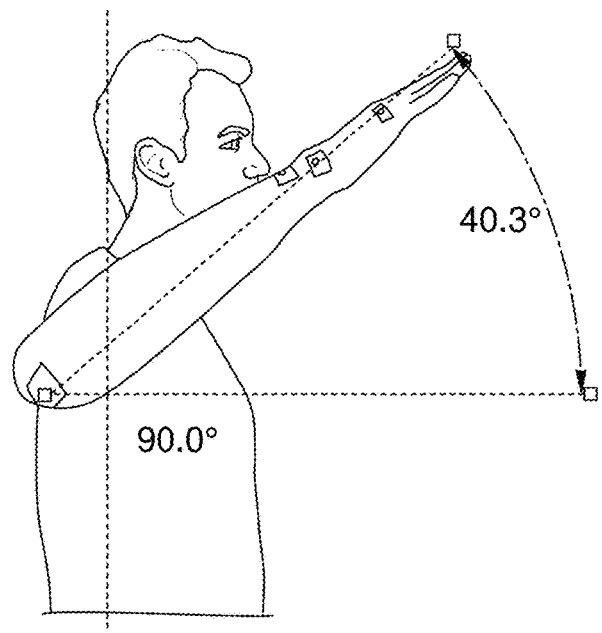
Figure 8C:
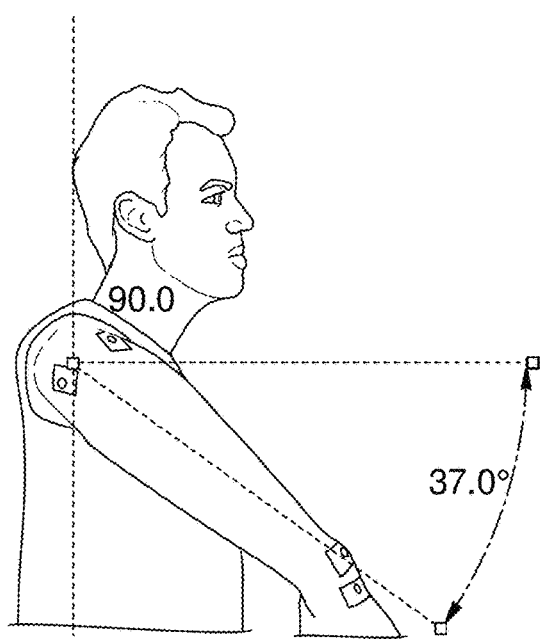
Figure 9A:
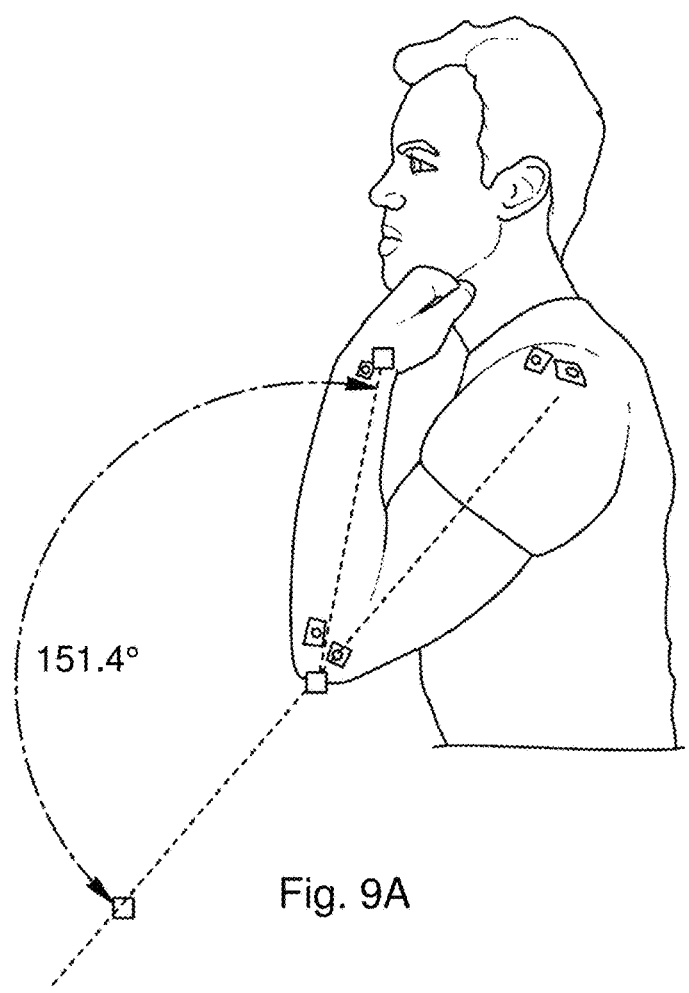
Figure 9B:
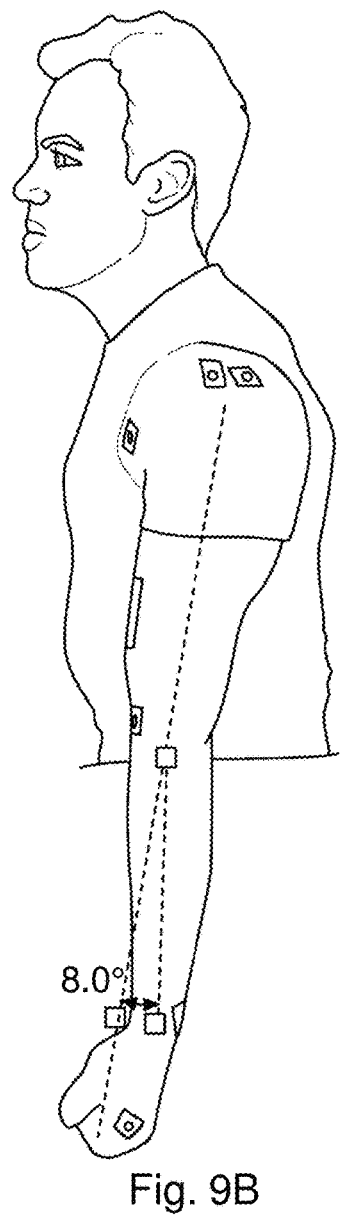
Figure 10A:
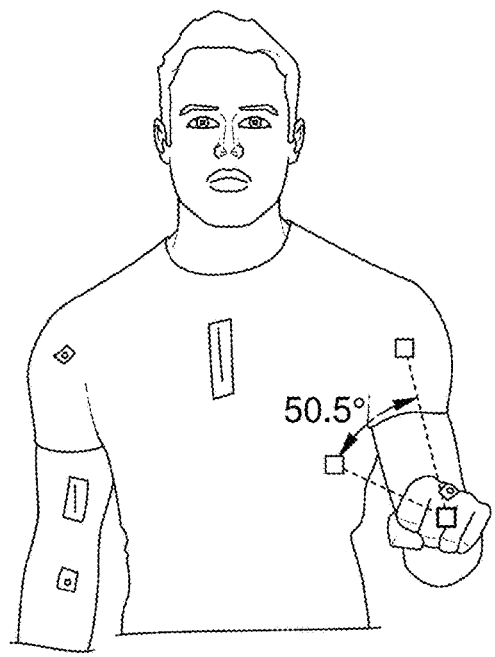
Figure 10B:
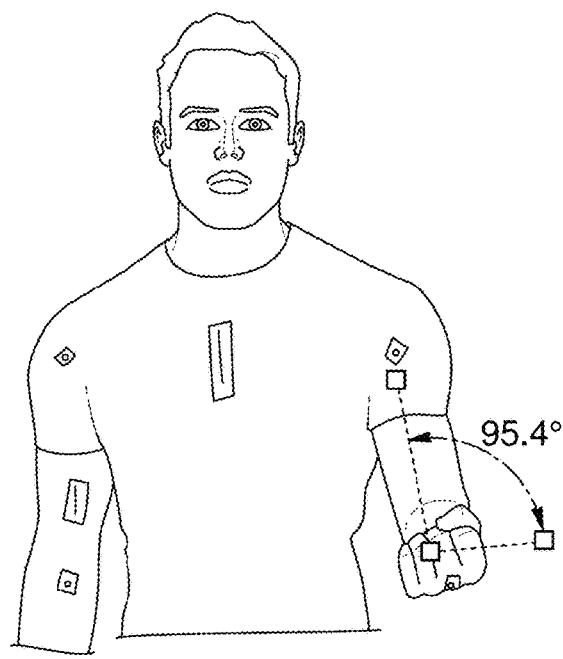
Figure 11A:
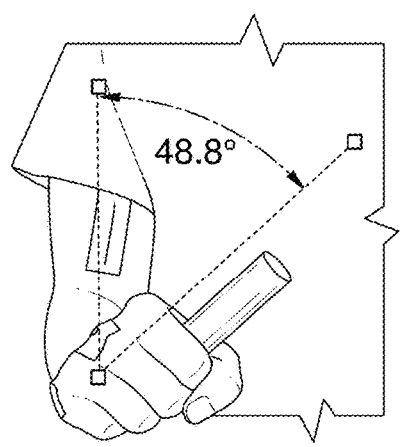
Figure 11B:
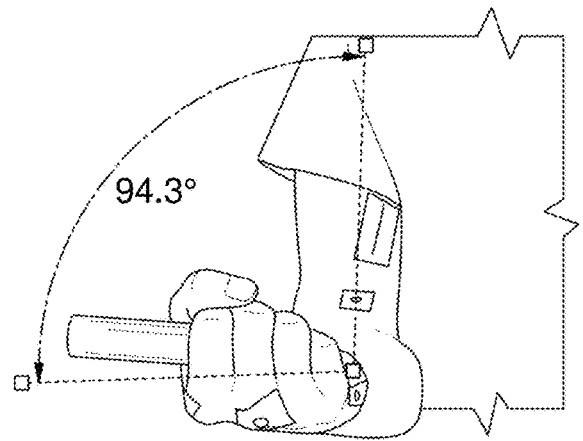
Figure 12A:
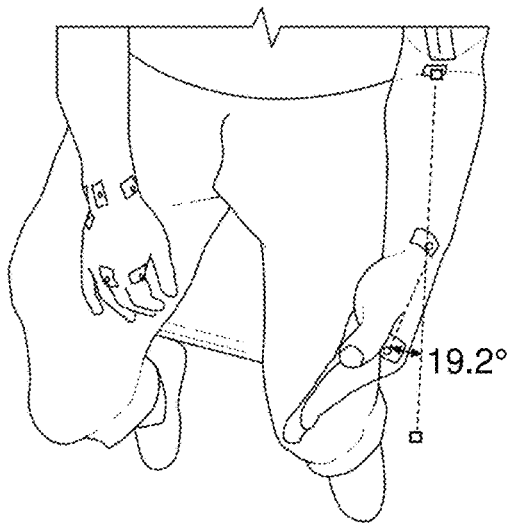
Figure 12B:
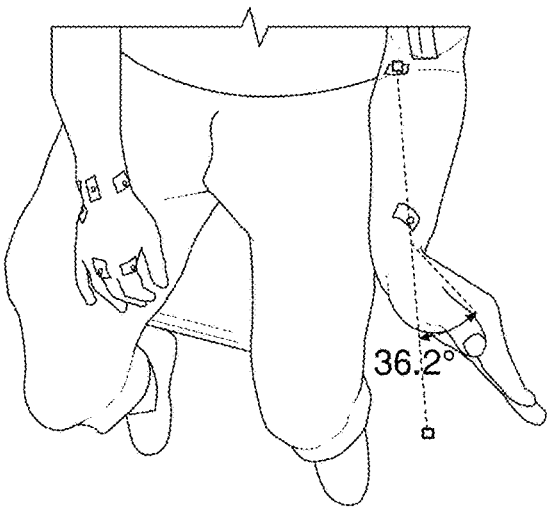
Figure 12C:
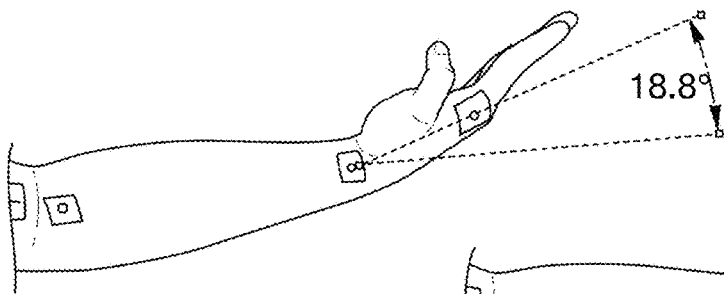
Figure 12D:
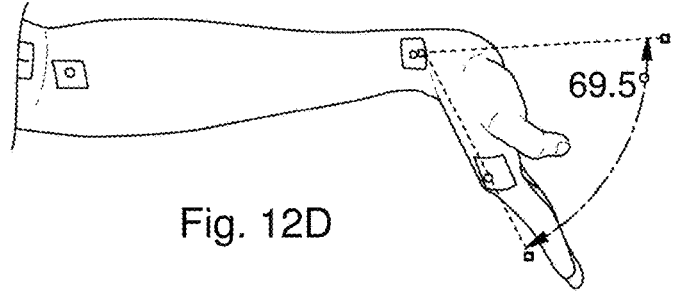
Figure 12E:
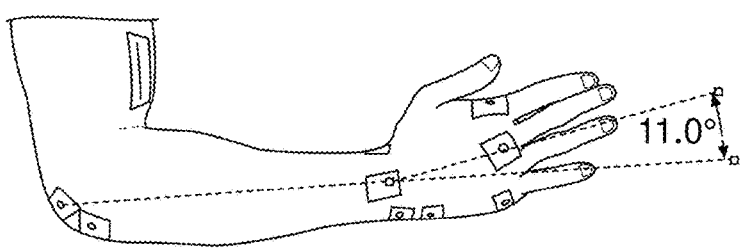
Figure 12F:
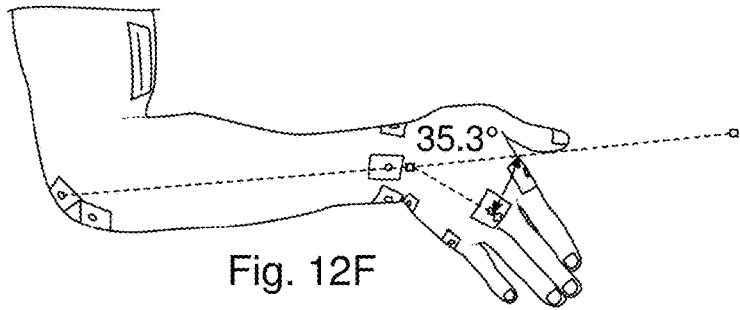

The CCs and CFs are distinguishable as having slidable layers in the deep fascia region. An illustration of two CCs is shown in FIG. 4. A cross-section of a region where a CC is present shows deep fascia layers which can slide relative to each other (as illustrated in FIGS. 3A and 3B). The two CCs in FIG. 4 correspond with the CCs identified as la-cx and la-pv in FIGS. 1A and 1B. Hyaluronic acid is present between the layers of the fascia and contributes to the ability of the fascial layers to slide relative to each other. In contrast, a similar cross-section from an area where no CCs are present shows the deep fascia layers are fused so that the layers lack the ability to slide relative to each other (FIG. 4).

The present disclosure entails the injection of hyaluronidase at or near the CC sites or CF sites. Thus, injections can be performed in a region within about a 1 inch diameter around CCs or CFs to relieve densification of the fascia and restore ease of movement. In embodiments, injections can be performed in a region within about a 0.75. 0.5 or 0.25 inch diameter around the CCs or CFs. We have observed that the amount of hyaluronidase useful in the present method is higher than what is typically used for adjuvant or dispersion purposes. For example, hyaluronidase can be administered at dosages of 25 USP units to 300 USP units per injection (and all dosages to the tenth decimal point there between).

The terms "unit" or "units" as used herein are intended to be the same as indicated on the commercially available products.

Further details of the commercially available Hylenex are provided in U.S. Pat. No. 7,767,429—incorporated herein by reference. The amount of hyaluronidase may be present in a suitable volume for injection. For example, in one embodiment, the dosage is 37.5 units (0.25 cc) to 300 units (2 cc) per site (CC) injected at desired sites, such as at 6-10 sites in the limb at various points along the limb at one or more centers of coordination.

In the method of the present disclosure, the CC sites for injection are selected based on the affected movement. For example, if restriction of movement of a joint is observed in the frontal plane, then hyaluronidase injections may be carried out at one or more CCs sites identified as circles in FIGS. 1A and 1B. If movement is restricted in the sagittal plane, then injections can be performed into one or more CC sites identified as diamonds (an and re points), and if movement is restricted in the horizontal plane, then injections may be performed into one or more CC sites identified as triangles (ir and er points), and if movement is restricted in the frontal plane, the injections can be performed into one or more CC sites identified as circles (me and la points). In the same manner, if movement is restricted in the ante-lateral and retro-lateral direction, then injections can be performed into one or more CF sites identified as diamonds (an-la and re-la points), and if movement is restricted in the ante-medio and retro-medio direction, then injections may be performed into one or more CF sites identified as triangles (an-me and re-me points). In some embodiments, corresponding CCs on the anterior and posterior are selected. Such embodiments have been found to advantageously provide a balancing effect on the fascia. Depending upon the restriction of movement, a combination of CCs in one or more of the frontal, sagittal, and horizontal planes may also be used. For example, if movement of the wrist (carpal joint) is restricted in all planes, the CCs to be injected may include an-ca, re-ca, ir-ca, er-ca, la-ca and me-ca.

More commonly, the restriction may be in multiple joints along a single plane. If the elbow joint is exhibiting stiffness in the sagittal plane, then multiple CC sites may be selected in the same plane across multiple joints. For example, the CC sites injected could include an-sc, an-hu, an-cu, an-ca, re-hu, re-cu, and re-ca. As another example, if an individual presents stiffness in knee movement (i.e., movement in the sagittal plane), then CC sites an-cx, an-ge, an-ta, re-ge and re-ta may be injected. As another example, if an individual presents stiffness in neck movement (i.e., movement in the retro-lateral direction), then CFs sites an-la-cl, an-la-sc, re-la-cl and re-la-sc may be injected.

The abbreviations used in the figures and in the description are as follows—an: ante (front), re: retro (back), ir: internal rotation, er: external rotation, me: medial, la: lateral, sc: scapular (shoulder), hu: humerus (upper arm), cu: cubitus (elbow), ca: carpus (wrist), cx: coxa (hip), ge: genu (knee), ta: talus (lower leg), cl: collum (neck), di: digiti (fingers), cp: caput (head), the thorax (trunk), pe: pes (foot), pv: pelvis, lu: lumbi (lumbar).

Based on the CC and CF site map provided herein, it is within the purview of those skilled in the art to identify which and how many sites to select for hyaluronidase injection.

It should be noted that the examples herein are non-limiting, and CCs may be selected based on the presentation of each patient.

It was observed that a one-time injection in specific sites resulted in relief of muscle stiffness for at least about 1 month and often longer with facilitation of passive and/or active mobility. In cases of spasticity the injections may be repeated. Exercise therapy to restore passive or active movement in normal planes will facilitate prolonged effect of the injections.

Hyaluronidase may be administered by any means that will deliver the agent to the relevant site. For example, Hyaluronidase may be injected locally into the stiff areas of the connective tissue. Injection (such as using a syringe) into the deep fascia region is within the purview of those skilled in the art. Surface anatomy maps indicate the depth of the points with respect to the skin surface, and the resistance in the tissue upon injection indicates that the area of stiffness has been reached: a grabbing of the needle is often felt in areas that are particularly stiff. Hyaluronidase may also be translocated transdermally using iontophoresis or sonophoresis in areas where the skin is thin, and the fascia more superficial. Iontophoresis utilizes small electric currents to enhance transport across the skin by mechanisms such as electrophoretic and electro-osmotic driving forces. Sonophoresis uses ultrasound as a physical enhancer for systemic drug delivery, and can effectively deliver Hyaluronidase alone or in combination with other agents regardless of their electrical characteristics. It can also be coupled with iontophoresis and microneedling methods to enhance drug delivery.

Sonophoresis can be used at frequencies in the range of 20 kHz-16 MHz and intensities up to 14 W/cm$^2$ (spatial average pulse average intensity, $I_{SAPA}$) to enhance skin permeability. Low frequency sonophoresis (20 kHz<f<100 kHz) may be particularly useful. Sonophoresis may be directed by ultrasound guidance to areas where the connective tissue shows reduced elasticity.

The hyaluronidase formulations may comprise other ingredients such as non-active ingredients. For example, the formulations may comprise excipients such as Azone (1-dodecylazacycloheptan-2-one or laurocapram), DMSO (dimethyl sulphoxide), and/or surfactants. Such excipients may increase transdermal drug transport via several mechanisms such as increased drug solubility in the donor formulation and drug partitioning into the subcutaneous space because of the solvent properties of these compounds. For example, DMSO, a commonly used topical analgesic, anti-inflammatory, and antioxidant, has been used in studies of skeletal muscle as a selective antioxidant or as a solvent for numerous drugs. Local anesthetic agents such as lidocaine can be combined with hyaluronidase when there is substantial pain. This may facilitate post-injection stretching for areas that are already slightly contracted. Sodium Bicarbonate may be used to increase onset time and prolong the action of hyaluronidase. Saline can be used with hyalruonidase to produce a volume effect and facilitate separation of the layers of the fascia. In one embodiment, the only enzyme in the administered composition is hyaluronidase. In one embodiment, the only protein in the composition is hyaluronidase.

In one embodiment, the individual exhibiting muscle stiffness is treated with only hyaluronidase. In one embodiment, the individual is not treated with benzodiazepines, baclofen, tizanidine hydrochloride, and dantrolene, or botulinum toxin type A or B. In one embodiment, an individual may be treated with other agents such as benzodiazepines, baclofen, tizanidine hydrochloride, dantrolene in addition to the hyaluronidase treatment. Botulinum toxin injections may be given after the effect of the hyaluronidase injections has worn off, but not during, to prevent systemic dispersion of the toxin.

Muscle stiffness may be assessed by standard means well known to clinicians and others skilled in the art. For example, the limitation in pain-free passive or active range of motion at a particular joint (Norkin and White 1995, Measurement of Joint Motion: A Guide to Goniometry. Philadelphia, Pa.: FA Davis Co) may be used. Spasticity or the resistance to passive movement may be assessed using the modified Ashworth scale (Bohannon, R. and Smith, M. 1987, Physical Therapy, 67(2): 206; Brashear et al., 2002, Archives of physical medicine and rehabilitation, 83(10): 1349-1354). Individuals may be asked to perform various joint movements and their performance may be evaluated. In one embodiment, their performance may be recorded on video and analysis can be carried out using commercially available software (such as Dartfish software).

The present method may be used to restore movement in the limbs and enhance limb function by releasing stiffness in the fascia and muscle caused by prolonged immobility secondary to disuse, orthopedic injury, neurologic causes of paralysis such as stroke, traumatic brain injury, multiple sclerosis, spinal cord injury, cerebral palsy or developmental causes of contractures, such as specific subtypes of arthrogryposis multiplex congentia, as well as muscle pain and joint stiffness from non-neurologic causes such as from prolonged bed rest, post-operative stiffness, myofascial pain and fibromyalgia, over-use, repetitive trauma, age-related muscle stiffness and muscle-stiffness due to diabetes.

In one embodiment, additional active ingredients, such as pain killers, anesthetics and the like may be used.

In one embodiment, the hyaluronidase injections are used to restore range of motion without causing further muscle paralysis (which occurs with botulinum toxin), cognitive and systemic effects (which occur with central nervous depressants such as baclofen, tizanidine, benzodiazepines etc.).

The injections may be used to preserve and restore range of motion without surgery in case of subtle contractures for which there is currently no treatment other than stretching and serial casting which can cause prolonged discomfort and may be ineffective if not sustained.

An application of the invention is as a minimally-invasive local injection at one or more CCs to treat limitation in movement and pain due to muscle stiffness, spasticity and mild contracture after neurologic injury such as stroke, spinal cord injury, traumatic brain injury, cerebral palsy, and multiple sclerosis.

Another application is in the treatment of muscle stiffness due to prolonged immobility from medical conditions requiring prolonged bed rest or orthopedic conditions such as fractures, and surgery.

Another application is in the treatment of muscle and joint pain and stiffness from traumatic and post-surgery causes, myofascial pain, non-specific musculoskeletal pain, paratendonitis, periarthritis, Chronic Regional Pain Syndrome, fibromyalgia, frozen shoulder, nerve entrapment and cheiroarthropathy (e.g. from diabetes).

Another application is to treat muscle contractures that occur due to reduced mobility in-utero or immediately after birth such as arthrogryposis multiplex congenita and brachial palsy from birth trauma.

Another application is to treat mild contractures and spasticity occurring from rare diseases such as but not limited to amyotrophic lateral sclerosis, hereditary spastic paraplegia, mucopolysaccharidosis, spinal muscular atrophy, and Rett syndrome.

The present method may be used in any animal. In one embodiment, the individual is a human being. In one embodiment, the individual is a non-human animal. It is generally considered that if the recipient is a human, the formulation will contain human hyaluronidase as the active agent. Similarly, for a given animal, preferably, hyaluronidase formulations comprising the active agent from the same species may be used. Based on the present disclosure locations of centers of coordination and/or center of fusion may be identified in animals for administration of hyaluronidase. The dosage may be determined empirically based on the site of the injection and extent of stiffness or using a more objective measure of muscle stiffness such as an elastogram using ultrasonography. Determination of the dosage is within the purview of those skilled in the art. Although hyaluronidase is known to be a short-acting drug (its activity is lost after about 12 hours), it was surprising that the patients treated with the present method reported reduced muscle stiffness as observed by increased range of motion, ease of movement, and the presence of reduced number of movements that generate pain after 2 days which lasted for at least about 1 month. It was observed that any inflammation that results from the injections subsides in about 2 days.

In one aspect, this disclosure provides kits. The kits comprise one or more of the following: one or more doses of hyaluronidase for administration (either in ready-to-use form or in a form that needs to be reconstituted), reconstitution medium (such as sterile saline, phosphate or other physiological buffers, water and the like), administration aids (such as syringes and the like), one or more charts showing centers for coordination and/or centers of fusion for administration of hyaluronidase, and instructions for use. The chart may identify all the CCs and CFs or may identify CCs and CFs as being in specific planes (sagittal, frontal and/or horizontal) in the front of the body and at the back of the body for restrictions in arm movement, leg movement, upper back problems, lower back problems and the like. In one embodiment, the kit comprises one or more of the following: 2-20 combined or individual doses of hyaluronidase, reconstitution medium for the hyaluronidase, charts providing locations for centers for coordination/centers of fusion in the body, and instructions for use such as instructions for reconstitution of the drug, audio and/or visual aids with instructions on assessing range-of-motion, selection of CC-sites based on the restrictions noted on assessment of movement, a guide for amount to be injected based on the size of the individual, and/or instructions for an exercise program to be performed after the injections are given. In one embodiment, the kit comprises 2-20 combined or individual doses of from 25-300 units (per dose) of hyaluronidase and a chart (such as FIGS. 1A-1B and/or 2A-2B) providing centers of coordination or center of fusion points. In one embodiment, the kit may be specific for a certain area. For example, the kit may contain from 2-20 combined or individual doses of hyaluronidase, reconstitution medium, and a chart showing the CC and/or CF sites for a certain area—such as the upper limb, shoulder upper back, neck and head, lower back and inferior limbs. In one embodiment, the individual doses are provided in ready to use syringes. The kits may be stored in the refrigerator or room temperature (or any temperature therebetween).

Example 1

This example describes the clinical use of a hyaluronidase formulation on 6 patients with chronic upper limb spasticity from a stroke (mean time since stroke was 5 years, range was 3-7 years). All the patients presented with moderate spasticity as assessed with the Modified Ashworth Scale (mean score was 3). Patients were selected because they had exhausted all current options.

The patients presented with lack of full pain-free range of motion pre-injection as evaluated by measuring their passive range of motion (Norkin and White, A Guide to Goniometry. Philadelphia, Pa.: FA Davis Co, 1995), from videos using Dartfish video analysis software (version 3.0.2). The videos were taken in a standard manner with the camera placed perpendicular and at a distance of 1 meter from the joint evaluated. Illustrations of video images are shown in FIGS. 5A-5B, 6, 7A-7C, 8A-8C, 9A-9B, 10A-10B, 11A-11B, and 12A-12F and results are provided in table 1.

Prior to the procedure a preliminary skin test for hypersensitivity to Hylenex recombinant was performed. An intradermal injection of approximately 0.02 mL (3 Units) of a 150 Unit/mL solution was injected. No erythema, itching or wheal were noted at 5 or 20 minutes.

Dilution: 1:1 dilution with normal saline: 3 ml of hyaluronidase ws combined with 3 ml of normal saline. 6 injections of 1 ml each of hylenex plus normal saline (Hylenex was 0.5 mls) were administered into 6 separate fascial areas.

Location of Injections: the locations of the injections were selected during the clinical assessment as 6 fascial areas in the upper limb that showed the greatest stiffness and appeared to be limiting motion at the corresponding joints in each patient. The six sites were selected from the following

TABLE 1

| | Normal range of motion in degrees | Pre-injection degrees (SE) | Day 2 degrees (SE) | Follow-up degrees (SE) |
|---|---|---|---|---|
| Shoulder | Flexion (movement of the arm forward) (0-180) | 116 (7.57) | 129 (6.83) | 137 (6.61) |
| | Abduction (raising the arm up to the side) (0-180) | 117 (6.06) | 145 (11.39) | 155* (10.00) |
| Elbow | Flexion (bending the elbow) (0-160) | 127 (3.75) | 133 (4.16) | 128 (4.23) |
| | Extension (straightening the elbow) (90-180) | 171 (3.42) | 172 (5.16) | 174 (3.46) |
| | Pronation (forearm rotation to face palm down) (0-100) | 85 (7.90) | 94* (6.39) | 97* (3.48) |
| | Supination (forearm rotation to face palm up) (0-90) | 70 (12.39) | 90* (8.31) | 89* (13.04) |
| Wrist | Flexion (bending the wrist down) (0-90) | 69 (6.98) | 70 (7.42) | 61 (7.47) |
| | Extension (bending the wrist up) (0-70) | 31 (3.90) | 56* (8.32) | 46* (3.31) |
| | Ulnar deviation (pulls the hand toward the midline of the body) (0-65) | 40 (3.94) | 44 (2.54) | 44 (1.22) |
| | Radial deviation (pulls the hand away from the midline of the body) (0-25) | 15 (5.19) | 22 (4.40) | 20 (3.32) |

Table 1: Mean range of motion across 6 subjects pre-injection, 2 days post-injection and at approximately 4-6 week follow up. Statistically significant differences compared to pre-injection values. The comparisons were made using Wilcoxon matched-pairs signed rank test.

The majority of the patients presented with limited passive range of motion pre-injection in the following joints: wrist extension (59% less than normal range of motion); ulnar deviation (43% less than normal range of motion); shoulder abduction (37% less than normal range of motion); shoulder flexion (36% less than normal range of motion); elbow flexion (26% less than normal range of motion); wrist flexion (25% less than normal range of motion); and forearm supination (23% less than normal range of motion).

sites depending on individual presentation: an-sc, an-cu, re-cu, ir-cu, me-cu, la-cu, la-ca, it-ca, and re-ca.

Summary of Outcome: At two-day follow up, the patients reported increased range of motion in most of the joints targeted by the injections. The increase in passive range of motion is shown in table 1. The patients who had active movement capability also showed an increase in the active range of motion.

The patients showed a statistically significant increase in range of motion for forearm pronation and supination and wrist extension 2 days post-injection, and for shoulder abduction, forearm pronation and supination and wrist extension at follow-up. The comparisons were made using Wilcoxon matched-pairs signed rank test.

The movements that did not show an improvement were because there was little limitation in initial range of motion at these joints (table 1), and because we limited the location of the injections to 6 most impaired and painful areas for this cohort. An example of a patient treated with this is provided in Example 2 below.

Example 2

Problem: A 58 year old male patient sustained a stroke 2 years earlier and had severe pain and restriction of passive range of motion in his right upper limb. The pain was a complaint and described subjectively by the patient. Objectively, the patient could not tolerate passive movements in the shoulder, elbow and wrist joints due to pain. There were no signs of joint or skin inflammation. There had been no improvement in his neurologic or functional status despite the use of oral medications and Botulinum toxin injections.

Prior to the procedure a preliminary skin test for hypersensitivity to HYLENEX recombinant was performed. An intradermal injection of approximately 0.02 mL (3 Units) of a 150 Unit/mL solution was injected. No erythema, itching or wheal were noted at 5 or 20 minutes.

Dilution: 1:1 dilution with normal saline: 3 ml of hyaluronidase with 3 ml of normal saline was prepared for administration.

Dedicated Physical Exam: Passive range of motion at the shoulder, elbow, forearm, wrist and fingers of the right upper limb were recorded. The tone during passive range of motion was severe according to the Modified Ashworth Scale (MAS) as indicated in table 2 below. The MAS is the most common and frequently used measure of spasticity in adults and children, both in research and clinical practice (Bakheit et al 2003, J Neurol Neurosurg Psychiatry, May, 74(5):646-8. PubMed PMID: 12700310). MAS was proposed by Bohannon and Smith in the 1987 and spasticity is rated on a scale from 0-4 as shown in Table 2.

TABLE 2

Modified Ashworth Scale rating score

| Grade | Description |
|---|---|
| 0 | No increase in muscle tone |
| 1 | Slight increase in muscle tone, manifested by a catch and release or b minimal resistance at the end of the ROM when the affected pasr(s) is moved in flexion or in extention |
| 1+ | Slight increase in muscle tone, manigested by a catch, followed by minimal resistance throughout the remainder (less than half) of ROM |
| 2 | More marked increase in muscle tone, throughout most of the ROM, but affected part(s) easily moved |
| 3 | Considerable increase in muscle tone, passive movement is difficult |
| 4 | Affected part(s) rigid in flexion or extension |

The right arm could be externally rotated at the shoulder but shoulder flexion and abduction were limited to 90 degrees and were extremely painful. The right arm could be fully extended at the elbow. The wrist could be brought to neutral. However the forearm could not be supinated and the wrist could not be extended past neutral due to subjective reports of pain.

All injected areas were cleaned with chloroprep swabs prior to injecting.

Units used were 150 units per ml.

Location of Injections: 6 injections of 1 ml each of hylenex plus normal saline (hylenex was 0.5 mls) were injected into the areas described in table 3 at CCs an-sc, re-cu, an-ca, la-ca, re-ca, ir-cu

TABLE 3

| | Side | Modified Ashworth score | Volume (cc) | # Units |
|---|---|---|---|---|
| SHOULDER | | | | |
| In the clavi-coraco-axillary fascia, that unites the monoarticular (pectoralis minor) and biarticular (pectoralis major) muscle fibers (an-sc). | R | 3 | 1 | 75 |
| UPPER ARM | | | | |
| Over the fascia around the belly of triceps at the level of deltoid's distal tendon (re-cu) | R | 3 | 1 | 75 |
| LOWER ARM | | | | |
| In the antebrachial fascia, in the point where the monoarticular (flexor carpi radialis) and biarticular (flexor pollicis longus) muscle fibres unite (an-ca) | R | 3 | 1 | 75 |
| In the fascia around the extensor carpi radialis (la-ca) | R | 3 | 1 | 75 |
| Between the extensor digitorum and extensor pollicis longus (re-ca) | R | 3 | 1 | 75 |
| In the fascia around the pronator teres (ir-cu) | R | 3 | 1 | 75 |

Table 3: Treatment protocol for patient 1.

Summary of Procedure: The patient tolerated the procedure well. Hemostasis was achieved. The patient left the office in stable condition. Post-injection precautions were reviewed with the patient. He was advised to use warm compress for soreness related to injections. He was told to resume normal activity and the caregiver was advised to stretch his arm frequently.

Summary of Outcome: The injections had a dramatic effect on the patient on day 2. He was able to tolerate shoulder abduction to 90° for a prolonged period. Previously we were unable to achieve that degree of motion secondary to extreme pain reported subjectively. His therapist created a simple positioning device for him to maintain the position at the shoulder and provide a slow stretch. The patient's spasticity decreased from Ashworth score of 3 to 1 at all the joints in two days.

These data demonstrate the effectiveness of the present method.

Example 3

This example provides further illustration of this method.

Problem: A fifteen year old boy sustained a basketball injury to the neck which led to a stroke 8 months ago with severe muscle stiffness and lack of passive and active range of motion in his right upper limb. He received hyaluronidase injections for the first time 3 months which led to dramatic improvement in shoulder range of motion both passively and actively. However the wrist and hand were not addressed at that time. Objectively, the patient kept the fingers of his right hand curled and maintained the wrist in a flexed position. Passive movements were painful as they needed to be forced. There were no signs of joint or skin inflammation. Other modalities including oral medication, therapeutic exercise and stretching did not relieve the tightness in the wrist and hand.

Prior to the procedure a preliminary skin test for hypersensitivity to HYLENEX recombinant was performed. An intradermal injection of approximately 0.02 mL (3 Units) of a 150 Unit/mL solution was injected. No erythema, itching or wheal were noted at 5 or 20 minutes.

Dilution: 1:1 dilution with normal saline: 4 ml of hyaluronidase with 4 ml of normal saline was prepared for administration.

Dedicated Physical Exam: Active and passive range of motion at the shoulder, elbow, forearm, wrist and fingers of the right upper limb were recorded. The tone during passive range of motion was severe according to the Modified Ashworth Scale (MAS) as indicated in table 4 below.

Full active range-of-motion at the shoulder and elbow and forearm supination were recorded. Active range-of-motion was restricted for forearm pronation, wrist extension and finger extension. Specifically, range of motion for pronation was 90-45 degrees, there was no active motion at the wrist and the fingers could not be extended fully at the proximal inter-phalangeal joints passively or actively.

All injected areas were cleaned with chloroprep swabs prior to injecting.

Units used were 150 units per ml.

Location of Injections: 8 injections of 1 ml each of hylenex+normal saline were injected into the areas described in table 4 at CCs la-cu, ir-ca, an-ca, me-cu, re-ca, ir-cu, re-di, er-di, ir-di.

TABLE 4

|  | Side | Ashworth | Volume (cc) | # Units |
| --- | --- | --- | --- | --- |
| LOWER ARM | | | | |
| In the fascia around the brachioradialis (la-cu) | R | 2 | 1 | 75 |
| In the fascia around the flexor digitorum (ir-ca) | R | 3 | 1 | 75 |
| In the fascia around the flexor carpi radialis (an-ca) | R | 3 | 1 | 75 |
| In the fascia around the flexor carpi ulnaris (me-cu) | R | 3 | 1 | 75 |
| Between the extensor carpi ulnaris and the extensor digitorum (re-ca) | R | 3 | 1 | 75 |
| In the fascia around the pronator teres (ir-cu) | R | 2 | 1 | 75 |
| HAND AND WRIST | | | | |
| In the dorsal aspect of the hand between the metacarpal bones (re-di, er-di); 2 sites | R | 3 | 1 | 75 |
| In the palmar fascia (ir-di) | R | 3 | 1 | 75 |

Table 4: Treatment protocol for patient 2.

Summary of Procedure: The patient tolerated the procedure well. Hemostasis was achieved. The patient left the office in stable condition. Post-injection precautions were reviewed with the patient. He was advised to use warm compress for soreness related to injections. He was told to resume normal activity and given a home exercise program to stretch the forearm, wrist and fingers.

Summary of Outcome: The injections had a dramatic effect on the patient examined 1 week later. Forearm pronation was observed to have full active pronation with some shoulder strategy; previously 90 to 45 degrees. Wrist extension was from 80 degrees of flexion to slightly past neutral. Wrist flexion was 0-80 passive, some active with gravity assist. Finger flexion-extension (MCP) was 90-0 degrees with PIP's extended (MAS=1). He could keep the fingers extended at rest and fold the hands together in praying position. The Ashworth score decreased from 3 to 1 for the greatest areas of muscle stiffness.

These data demonstrate the effectiveness of the present method.

While the method has been described through specific embodiments, routine modifications will be apparent to those skilled in the art, which modifications are intended to be within the scope of the disclosure.

The invention claimed is:

1. A kit for reducing muscle stiffness comprising:
   a) one or more ready-to-use syringes, each syringe comprising two or more doses of hyaluronidase and one or more ingredients chosen from 1-dodecylazacycloheptan-2-one, laurocapram, dimethyl sulfoxide, a surfactant, lidocaine, sodium bicarbonate, and combinations thereof, wherein each dose comprises from 25-300 USP units of hyaluronidase; and
   b) optionally, one or more charts depicting centers of coordination and/or centers of fusion, said centers of coordination or centers of fusion providing sites for administration of the hyaluronidase,
   wherein delivering hyaluronidase in a region of deep fascia surrounding a first muscle or in a region of deep fascia surrounding a second muscle that affects the function of the first muscle at or near one or more centers of coordination or center of fusion associated with the first muscle, second muscle, or a combination thereof, results in reduction of stiffness of the first muscle.

2. The kit of claim 1, further comprising instructions for use of the charts and/or delivery of hyaluronidase.

3. The kit of claim 1, wherein each dose is 37.5 to 300 USP units of hyaluronidase.

4. The kit of claim 1, wherein each syringe comprises from 2 to 20 doses of hyaluronidase.

5. A ready-to-use syringe comprising two or more doses of hyaluronidase and one or more ingredients chosen from 1-dodecylazacycloheptan-2-one, laurocapram, dimethyl sulfoxide, a surfactant, lidocaine, sodium bicarbonate, and combinations thereof, wherein each dose comprises from 25-300 USP units of hyaluronidase.

6. The ready-to-use syringe of claim 5, wherein the syringe comprises from 2 to 20 doses of hyaluronidase.

7. A kit for reducing muscle stiffness comprising:
   a) one or more ready-to-use syringes, each syringe comprising one or more doses of hyaluronidase having a concentration of 75 Unit/mL and one or more ingredients chosen from 1-dodecylazacycloheptan-2-one, laurocapram, dimethyl sulfoxide, a surfactant, lidocaine, sodium bicarbonate, and combinations thereof, wherein each dose comprises from 25-300 USP units of hyaluronidase; and
   b) optionally, one or more charts depicting centers of coordination and/or centers of fusion, said centers of coordination or centers of fusion providing sites for administration of the hyaluronidase,
   wherein delivering hyaluronidase in a region of deep fascia surrounding a first muscle or in a region of deep fascia surrounding a second muscle that affects the function of the first muscle at or near one or more centers of coordination or center of fusion associated with the first muscle, second muscle, or a combination thereof, results in reduction of stiffness of the first muscle.

8. The kit of claim 7, wherein each syringe comprises from 2 to 20 doses of hyaluronidase.

9. The kit of claim 7, further comprising instructions for use of the charts and/or delivery of hyaluronidase.

10. The kit of claim 1, wherein the hyaluronidase is at a concentration of 75 USP/mL.

* * * * *